(12) United States Patent
Kahl et al.

(10) Patent No.: US 9,242,409 B2
(45) Date of Patent: Jan. 26, 2016

(54) METHOD OF MANUFACTURING A SAMPLE CHAMBER

(71) Applicant: ibidi GmbH, Martinsried (DE)

(72) Inventors: Valentin Kahl, Martinsried (DE); Elias Horn, München (DE)

(73) Assignee: ibidi GmbH, Martinsried (DE)

( * ) Notice: Subject to any disclaimer, the term of this patent is extended or adjusted under 35 U.S.C. 154(b) by 142 days.

(21) Appl. No.: 13/916,737

(22) Filed: Jun. 13, 2013

(65) Prior Publication Data

US 2014/0162350 A1 Jun. 12, 2014

(30) Foreign Application Priority Data

Jun. 15, 2012 (EP) .................................. 12172261

(51) Int. Cl.
| | |
|---|---|
| *B29C 65/78* | (2006.01) |
| *B01L 3/00* | (2006.01) |
| *C12M 1/22* | (2006.01) |
| *B29C 65/50* | (2006.01) |
| *B29C 65/00* | (2006.01) |
| *B29L 31/00* | (2006.01) |

(52) U.S. Cl.
CPC ................. *B29C 65/78* (2013.01); *B01L 3/508* (2013.01); *B01L 3/5085* (2013.01); *B29C 65/5057* (2013.01); *B29C 66/028* (2013.01); *B29C 66/112* (2013.01); *B29C 66/114* (2013.01); *B29C 66/1222* (2013.01); *B29C 66/1224* (2013.01); *B29C 66/53461* (2013.01); *B29C 66/71* (2013.01); *C12M 23/10* (2013.01); *B01L 2200/0689* (2013.01); *B01L 2200/12* (2013.01); *B01L 2300/0851* (2013.01); *B29C 66/7392* (2013.01); *B29C 66/73161* (2013.01); *B29C 66/7465* (2013.01); *B29K 2995/0072* (2013.01); *B29L 2031/712* (2013.01)

(58) Field of Classification Search
CPC ..... B29C 65/5057; B29C 65/78; B01L 3/508; B01L 3/5085; C12M 23/10
USPC ........... 156/272.2, 272.6; 422/552; 435/289.1
See application file for complete search history.

(56) References Cited

U.S. PATENT DOCUMENTS

| | | | |
|---|---|---|---|
| 6,033,605 A * | 3/2000 | Szlosek ......................... 264/1.7 |
| 2003/0021457 A1* | 1/2003 | Kirk et al. ..................... 382/133 |
| 2006/0118479 A1* | 6/2006 | Shevkoplyas et al. ..... 210/433.1 |
| 2009/0191621 A1* | 7/2009 | Zantl et al. ................. 435/305.1 |
| 2010/0136671 A1 | 6/2010 | Ogihara et al. |
| 2010/0303687 A1* | 12/2010 | Blaga et al. ................... 422/504 |

FOREIGN PATENT DOCUMENTS

DE 10159091 A1 6/2003

* cited by examiner

*Primary Examiner* — Daniel McNally
(74) *Attorney, Agent, or Firm* — IP Strategies

(57) ABSTRACT

The invention comprises a method of manufacturing a sample chamber, comprising the steps of: providing a first (20) and a second (30) component, the first component (20) comprising an elastomer; treating the elastomer in the region of a contact surface of the first component (20) and/or treating a contact surface of the second component (30) with a plasma, with plasma waste gas, and/or with a reactive gas; and connecting the contact surface of the first component (20) with the contact surface of the second component (30).

13 Claims, 9 Drawing Sheets

METHOD OF MANUFACTURING A SAMPLE CHAMBER

FIELD OF THE INVENTION

The present invention relates to a method of manufacturing a sample chamber and a sample chamber manufactured according to said method.

BACKGROUND OF THE INVENTION

In particular in the field of cell microscopy, most diverse forms of sample chambers are known. Almost all sample chambers include structures for receiving a sample, for example in the form of microfluidic channels or reservoirs. Examples of such sample chambers are shown in EP 1 886 792 A2, WO 2008/149914 A2, WO 2005/079985, or DE 101 48 210. Simple and well-known forms comprise Petri dishes and multiwell plates as they are described in DIN EN ISO 24998 or ANSI/SBS 2-2004 for microplates.

Possible application fields for such sample chambers are in particular the field of molecule or cell microscopy. The samples under test are placed into a reservoir of the sample chamber together with a liquid and can then be examined with high-resolution methods (for example transmitted-light microscopy, fluorescence microscopy, confocal microscopy, etc.)

Well-known sample chambers are typically made as single-component or multi-component chambers. Examples of single-component sample chambers are glass Petri dishes and multiwell plates of polystyrene (PS) which are made by injection molding. Multi-component sample chambers usually comprise at least one side wall and one bottom plate which are connected to each other by various methods. Above all, ultrasonic welding or gluing are well-known. One type of connection by adhesive or tacky layers is described, for example, in EP 1 886 792 A2.

As to manufacture, it is often advantageous to produce the sample chambers from several components or parts. A connection by ultrasonic welding, however, requires a lot of energy. The use of adhesive or tacky layers, however, often involves the use of solvents. The latter, however, are disadvantageous in that residues can lead to a contamination of the sample when the sample carrier is in use.

BRIEF SUMMARY OF THE INVENTION

It is therefore the object of the present invention to provide a method of manufacturing a sample chamber which permits to manufacture a two- or multi-component sample carrier without using solvents.

This object is achieved by a method according to claim 1.

The inventive method of manufacturing a sample chamber comprises the steps of:
providing a first and a second component, the first component comprising an elastomer,
treating the elastomer in the region of a contact surface of the first component and/or treating a contact surface of the second component with a plasma, with plasma waste gas, and/or with a reactive gas, and
connecting the contact surface of the first component with the contact surface of the second component.

The inventors of the present application found out that by treating a contact surface, which in particular comprises an elastomer, with a plasma, with plasma waste gas, and/or with a reactive gas, a surface can be provided which permits a permanent, solvent-free and liquid-tight connection of components. In other words, this permits a connection without adhesive and without adhesive layer.

By the connection of the contact surface of the first component with a contact surface of the second component, a liquid-tight connection between the components can be in particular produced. Thereby, the sample chamber can be used for examinations involving liquids.

By the connection of the contact surface of the first component with the contact surface of the second component, the components can be permanently connected. In other words, the components can be connected with each other so that they cannot be detached, or cannot be detached without destroying them. This means that a particularly stable sample chamber can be obtained thereby.

The contact surface of the first component means here a surface of the first component which is in contact with a surface of the second component after the components have been connected. Correspondingly, a contact surface of the second component means a surface of the second component which is in contact with the corresponding surface of the first component after the components have been connected.

The plasma can in particular be an atmospheric plasma or a corona. Here, atmospheric plasma means a plasma which is not ignited at subatmospheric pressure with respect to atmospheric pressure. It can in particular be an atmospheric plasma with nitrogen as the active gas. In case of a so-called corona, it can in particular be a corona treatment with ambient air as the active gas.

One or more ionized/activated gases which have been ionized or activated by an ignited plasma can be designated as waste gas of a plasma or plasma waste gas.

Gas having a high avidity, meaning that it has a high capacity of entering into a chemical reaction, can be designated as reactive gas. The reactive gas can be, for example, ozone or nitrogen oxides, or reactive gases containing oxygen, nitrogen and/or carbon as molecular components.

An elastomer is meant to be an elastically deformable plastic. The elastomer can in particular be a silicone, in particular polydimethylsiloxane (PDMS). The elastomer can also be an injection-molded elastomer-based silicone.

The elastomer can have a Shore A hardness of more than 40, in particular of 60 to 88. This can improve stability, in particular when it is gripped by a hand.

The first component can also consist of an elastomer. This permits a particularly easy manufacture of the sample chamber.

The second component can comprise a glass or consist of glass. The glass can in particular be borosilicate glass, quartz glass, or soda-lime glass. Combinations of different glasses are also conceivable.

The second component can in particular be coated with a glass. In particular, the second component may only be coated with glass in the region of the contact surface of the second component.

The second component can comprise a plastic. The plastic can in particular be COC (cyclic olefin copolymer), COP (cyclic olefin polymer), PE (polyethylene), PS (polystyrene), PC (polycarbonate), and/or PMMA (polymethylmetacrylate). In this case, the method can comprise the vaporization of the second component with a glass layer, in particular with $SiO_x$, in particular in such a way that the contact surface of the second component comprises a glass or consists of glass.

The second component can in particular be a plastic foil. A plastic foil can mean a sheet element of plastic whose longitudinal dimensions are early longer than its thickness.

As an alternative or in addition, the second component can comprise an elastomer, in particular a silicone, or a metal.

Independent of the basic material of the second component, the method can comprise the vaporization of the second component with a glass layer, in particular with $SiO_x$, in particular such a way that the contact surface of the second component comprises glass or consists of glass.

The inventors of the present application found out that a particularly advantageous connection can be obtained in particular between an elastomer treated with plasma, with plasma waste gas, and/or with a reactive gas, and a glass.

It moreover surprisingly showed that even in a case where only the glass is treated with plasma, with plasma waste gas and/or with a reactive gas, an adequate connection can be achieved.

The first component can be embodied to be mirror-symmetrical with respect to a plane of symmetry that is parallel to the contact surface of the first component. This can further facilitate the manufacture of the sample chamber as two equivalent orientations of the first component are available during the production process.

In this case, the first component can in particular consist of an elastomer.

The first component can moreover comprise a thermoplastic. The first component can in particular be a composite of a thermoplastic and an elastomer. A composite of a thermoplastic plastic (thermoplastic) and an elastomer can have a positive effect on stability. In particular, the thermoplastic can produce the required stability while the elastomer can compensate internal mechanical stresses. Such mechanical stresses can in particular occur due to thermal stresses, for example in steam sterilization (usually at about 121° C.). Moreover, the thermoplastic can improve the stability of the sample chamber when the latter is gripped by a hand.

The thermoplastic plastic or thermoplastic can in particular be COC, COP, PE, PS, PC, and/or PMMA.

The first component can in particular comprise two interconnected elements, a first element comprising the thermoplastic and a second element comprising the elastomer.

The first element can be made by injection molding. In other words, the method can comprise the manufacture of a first element from a thermoplastic by means of injection molding.

The first element can in particular consist of the thermoplastic.

The first element, however, can also comprise other materials or consist of other materials, for example of glass. In other words, the first component can comprise two interconnected elements, one of the elements comprising the elastomer.

The second element can comprise the elastomer or consist of the elastomer. The second element can be injection-molded to the first element in a two-component injection molding process.

The first component can in particular have a rectangular or circular base. The first element and the second element can then also have a rectangular or circular design, in particular where the second element is disposed at the bottom side or upper side of the first element.

The second component can correspondingly also have a rectangular or circular design.

The maximum or mean dimension of the second element in a direction perpendicular to the contact surface of the first component can amount to maximally 50%, in particular 1% to 20%, of the total maximal or mean dimension of the first component perpendicular to the contact surface of the first component. Thereby, the region where a sample in the sample chamber, in particular in the form of a liquid, will come into contact with the elastomer can be minimized. The elastomer can tend to absorb liquids or contain components that can diffuse into the liquid. By the minimization of the dimension of the second element, the risk of contamination can be prevented.

The first element can in particular have a maximal or mean dimension perpendicular to the contact surface of the first component of 1 cm or more than 1 cm. The second element can have a maximal or mean dimension perpendicular to the contact surface of the first component of less than 1 cm, in particular less than 1 mm.

The second element and/or the first component can also have a constant dimension. In this case, the maximal dimension is equivalent to the mean dimension is equivalent to the constant dimension.

A typical dimension of the first element perpendicular to the contact surface of the first component can be, for example, 2 cm, that of the second element 1 mm. If the second element is to be used as a septum, the dimension of the second element perpendicular to the contact surface of the first component can at least partially also be larger, in particular in the region of the second element to be used as a septum. In particular, the dimension of the second element perpendicular to the contact surface of the first component can also vary.

In a particular embodiment, elastomer elements that should only serve as a septum can also be integrated in the thermoplastic region of the first component. In other words, the first element can comprise regions which comprise an elastomer or consist of elastomer and adjoin a reservoir of the sample chamber which is formed by connecting the first and the second components. These regions can be partially or completely surrounded by regions of the first element which do not comprise any elastomer. In other words, these regions then do not have to be in contact with the second component any longer. These septa can have dimensions of 2 cm to 5 mm.

These regions can in particular directly adjoin the reservoir. The regions can in particular be continuous and connect the outer side of the reservoir with the inner side.

Such regions are also conceivable for sample chambers which have not been manufactured by the method described herein. For example, these regions can also be provided in sample chambers where the components are glued or welded to each other, or in single-component sample chambers.

The first component can form a side wall and the second component a bottom of a reservoir after they have been connected to each other. As an alternative, the first component can form a bottom and the second component a side wall of a reservoir after the first component has been connected to the second component.

A reservoir can here in particular mean a volume region of the sample chamber to be manufactured which is suited for receiving a liquid. For this, the reservoir can comprise at least one side wall and one bottom. It can be a reservoir that is open to the top, or a cavity.

By connecting the first and the second components, a reservoir can be obtained, where the first component forms a side wall or a bottom of the reservoir, where the first component comprises a first element and a second element connected thereto, where only the second element comprises the elastomer, and where the first element is arranged such that it at least partially covers or conceals the second element towards the reservoir. Thereby, the risk of contamination in the reservoir can be further reduced. In this case, the first element can in particular comprise a thermoplastic or consist of a thermoplastic. The first element can cover the second element in particular such that it directly contacts the second element. The first element can also be arranged such that it completely covers the second element towards the reservoir.

As an alternative or in addition, by the connection of the first and the second components, a reservoir can be obtained, where the first component forms a side wall or a bottom of the reservoir, where the first component comprises a first element and a second element connected thereto, where only the second element comprises the elastomer, and where the first element is arranged such that it at least partially covers or conceals the second element towards the reservoir. Thereby, possible damages of the elastomer can be prevented or reduced. In this case, the first element can in particular comprise a thermoplastic or consist of a thermoplastic.

The first element can in particular cover the second element such that it directly contacts the second element. The first element can also be arranged such that it completely covers the second element on the side facing away from the reservoir.

The first element can also be arranged such that it also covers or conceals a side wall of the second component at least partially, in particular directly. Thereby, the second element can also be at least partially protected from damages.

As an alternative or in addition to the treatment of the elastomer in the region of a contact surface of the first component, the method can comprise a treatment of the contact surface of the second component with a plasma, with plasma waste gas and/or with a reactive gas. It showed that a treatment only of the contact surface of the second component is also sufficient for a secure connection. However, both contact surfaces can also be treated. Thereby, the connection between the first and the second components can be further reinforced.

The method can comprise an irradiation of the contact surface of the second component with UV light. This permits a further improvement of the connection of the components. A simultaneous or successive irradiation with UV light and treatment with plasma/plasma waste gases/reactive gas can also be done.

The method can comprise cleaning the second component before connecting it, in particular in an ultrasonic bath with water, isopropanol, an acid and/or a caustic solution. This also permits to obtain a better connection between the components.

The connection of the contact surface of the first component with a contact surface of the second component can in particular comprise pressing the contact surface of the first component against the contact surface of the second component, in particular with a force of less than 20 N, in particular less than 5 N. Thereby, a secure connection between the components can be produced without the efforts of high mechanical forces. The manufacture of the sample chamber can be facilitated in particular by the low mechanical forces to be applied. In this respect, the inventors of the present application surprisingly found that a force of less than 20 N, in particular less than 5 N, can be sufficient for producing the secure connection.

The component which forms a side wall of a reservoir after it has been connected can comprise an edge, a protrusion and/or an indentation for placing a lid. Thereby, a secure seat of a lid can be ensured. The edge, the protrusion and/or the indentation can in particular be surrounding.

The method can moreover comprise the provision of a third component and the connection of the third component with the first component, in particular where the elastomer is treated with a plasma, with plasma waste gas and/or with a reactive gas in the region of a further contact surface of the first component before its connection. In other words, the third component can be connected to the first component in the same manner as the second component.

The third component can comprise one or several ones of the above mentioned features of the second component. In particular, a contact surface of the third component can be treated as described above for the contact surface of the second component before it is connected. The connection of the third component with the first component can comprise one or several ones of the above mentioned features for the connection of the first component with the second component.

The third component can, after it has been connected, for example form a cover plate of the sample chamber.

The first component can be embodied such that a part of the first component in which a part of the elastomer is arranged projects beyond a side face of the second component after the first component has been connected with the second component. Thereby, the second component can be protected from damages. This is in particular advantageous if the second component comprises a glass and consists of glass, and the manufactured sample chambers are to be stored as bulk material after their manufacture.

This part of the first component can in particular be embodied such that it extends in a direction perpendicular to the contact surface of the first component after it has been connected, in particular such that a side face of the second component is at least partially covered or overlapped. Thereby, an even better protection can be ensured. The side face of the second component can be in contact with the part of the first component, in particular in direct contact. As an alternative, the part of the first component can at least partially cover or overlap the side face of the second component at a distance.

In particular, the part can be embodied such that it projects, after it has been connected, beyond a side of the second component facing away from the contact surface of the second component. Thereby, an even better protection of the second component can be achieved.

The first component can form a side wall and the second component a bottom of a reservoir after they have been connected, where the first component projects beyond a side face of the second component and includes a step or elevation extending in a direction perpendicular to the contact surface of the first component, and the step or elevation covers or overlaps a side face of the second component at least partially, in particular at a distance. The step or elevation can also have a dimension perpendicular to the contact surface of the first component which is larger than the maximal or mean or constant thickness of the second component. Thereby, the step or elevation can project beyond the bottom side of the second component.

The second component can in particular be a cover glass with a (constant) thickness of 1 μm to 300 μm, in particular 100 μm to 200 μm. A sample chamber with such a second component, in particular as bottom plate, advantageously permits the application of inverse microscopy, in particular high-resolution microscopy.

The contact surface of the first component can be smooth, in particular without structural elements. In particular, the surface can be as smooth as a float glass. Thereby, the connection between the components can be improved.

The roughness of the contact surface of the first and/or the second component can be in particular lower than 1 nm, in particular lower than 0.5 nm. The roughness can be determined according to EN ISO 25178.

The thickness of the first component can vary. In particular, the thickness of the first component can be smaller than the mean thickness of the first component in a region which comprises at least one part of the elastomer or consists of at least one part of the elastomer. This region of the first component can in particular adjoin a reservoir after the connection of the first component with the second component. This region can then be suited as an access for a syringe, a hollow needle, or for introducing Luer-Lock connections. This region can in particular serve as a septum or a perforable membrane.

Said region can in particular directly adjoin the reservoir. It can in particular be continuous and connect the outer side of the reservoir with the inner side. Several such regions can also be provided.

In the region, the first component can in particular have a thickness of less than 2 mm, in particular less than 1 mm.

For example, samples can then be introduced into the reservoir through a needle, where the region of the first component simultaneously has the function of a septum.

In particular, the first component can comprise a first element and a second element connected thereto, the second element comprising the elastomer or consisting of the elastomer, and the second element having a smaller thickness than the first element in one or several regions adjoining the reservoir after the components have been connected. The first element can comprise one or several ones of the above mentioned features.

The method can in particular be a method of manufacturing a sample chamber with one or several reservoirs. In particular, 1, 12, 24, 48, 96, 364 or 1536 round or rectangular reservoirs can be formed. These can correspond to current standards, depending on their design.

The component that forms the bottom of a reservoir after it has been connected can also be coated or treated chemically or physically in the region of the bottom of the reservoir, so that optimal properties for cell growth are generated. Here, in particular NH, COOH, or other hydrophilic groups can be used. However, it can also be plasma-treated plastic. In other words, the component forming the bottom of a reservoir after it has been connected can be plasma-treated in the region of the bottom of the reservoir before the components are connected.

The sample chamber can also be produced by injection molding with direct injection onto a bottom plate. For this a bottom plate, e. g. a cover glass of a size 1, 5, is inserted into a mold. Here, a thermoplastic can be directly injected onto the bottom plate, where the bottom plate has been in particular treated or activated as described above. However, two-component injection molding processes can also be employed in combination with an inserted bottom plate.

The invention moreover provides a sample chamber for microscopic examinations obtained by an above-described method.

In other words, the invention provides a sample chamber for microscopic examinations, comprising a first and a second component, the first component comprising an elastomer, wherein the elastomer has been treated with a plasma, with plasma waste gas and/or with a reactive gas in the region of a contact surface of the first component, and/or wherein a contact surface of the second component has been treated with a plasma, with plasma waste gas and/or with a reactive gas.

In such a sample chamber, one can dispense with an adhesive or an adhesive layer. Thereby, a contamination of the sample with advert residues can be prevented.

The sample chamber, in particular the first and the second components, can have one or several ones of the above mentioned features.

BRIEF DESCRIPTION OF THE DRAWINGS

Further features and advantages of the invention will be illustrated below with reference to the exemplary figures. In the figures.

DETAILED DESCRIPTION OF THE INVENTION

Figure 1:
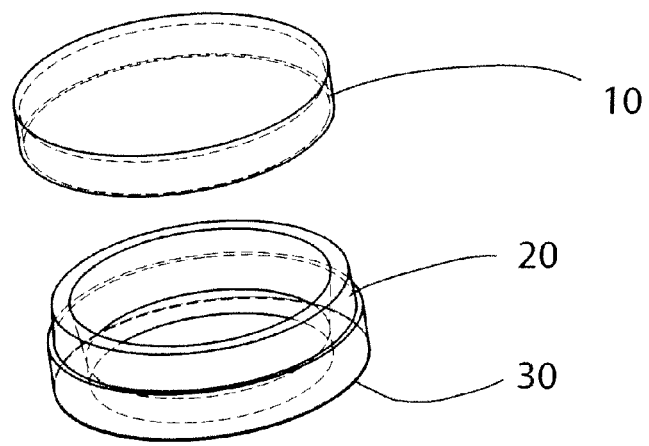
FIG. 1 shows a perspective view of an exemplary sample chamber.

FIG. 1 shows an exemplary sample chamber in a perspective representation. This sample chamber can be used, for example, for microscopic examinations, for example for fluorescence microscopy. The exemplary sample chamber comprises a first component 20 and a second component 30. In this example, the first component 20 consists of an elastomer, for example of a silicone, in particular of polydimethylsiloxane (PDMS).

The elastomer can also be an injection-molded elastomer-based silicone as it is distributed, for example, by the company Wacker Chemie AG under the name "Elastosil".

In this example, the second component 30 consists of glass, for example borosilicate glass, quartz glass or soda-lime glass.

As an alternative, the second component 30 could also be a plastic foil, that means a plastic element whose longitudinal dimensions are clearly longer than its thickness. This plastic foil could in particular consist of COC, COP, PE, PS, PC, and/or PMMA. This plastic foil could be completely or partially vaporized with a glass, in particular with $SIO_x$.

The first component 20 in this example has a contact surface in which the first component 20 is connected with the second component 30. The second component 30 has a corresponding contact surface.

The contact surface of the first component 20 has been treated, before it is connected with the second component 30, with a plasma, with plasma waste gas, and/or with a reactive gas. If the second component 30 is a glass-vaporized plastic foil, the glass is arranged at least in the region of the contact surface of the second component 30. The glass may also be arranged only in the region of the contact surface of the second component 30.

Since the elastomer has been treated with a plasma, with plasma waste gas and/or with a reactive gas in the region of the contact surface of the first component 20, a permanent, liquid-tight connection is produced between the first component 20 and the second component 30, said connection being formed without an adhesive or an adhesive layer. Thus, the connection between the components could be produced free from solvents. Moreover, no energy-consuming ultrasonic welding is necessary.

In other words, the sample chamber of FIG. 1 can be produced by the following method:

First, the first component 20 and the second component 30 are provided, the first component 20 consisting of an elastomer.

The elastomer is then treated with a plasma, a corona, an atmospheric plasma or with plasma waste gas and/or with a reactive gas in the region of a contact surface of the first component 20.

The contact surface of the first component 20 treated in this manner is then connected with a corresponding contact surface of the second component 30. The connection can comprise pressing the contact surface of the first component 20 against the contact surface of the second component 30, in particular at a low force of less than 20 N, in particular less than 5 N.

As an alternative or in addition, the contact surface of the second component 30 could also be treated with a plasma, a corona, an atmospheric plasma, or with plasma waste gas and/or with a reactive gas.

FIG. 1 moreover shows a lid 10 for closing a reservoir of the sample chamber. By such a lid 10, the evaporation of liquid from the reservoir can be avoided or at least reduced. Moreover, the lid can prevent or at least reduce a contamination of the sample from outside. Thereby, an internally sterile cell culture chamber, Petri dish or multiwell plate can be provided.

The first component 20 comprises a surrounding edge 60 for placing the lid 10. The surrounding edge 60 is designed such that the lid at least partially flatly lies against the lateral outer surface of the first component 20. The edge 60 can in particular have a width corresponding to the thickness of the material of the lid 10 in the region where it rests on the edge 60. One can achieve thereby that the lid 10 is aligned with the outer wall of the first component 20 after it has been placed. This permits an easier handling of the sample chamber. However, a non-aligned design is also conceivable.

Figure 2A:
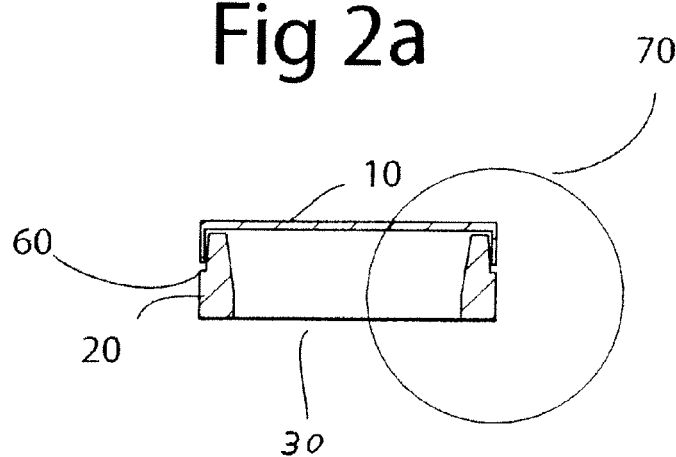
FIGS. 2a and 2b show cross-sectional views of the exemplary sample chamber of FIG. 1.
Figure 2B:
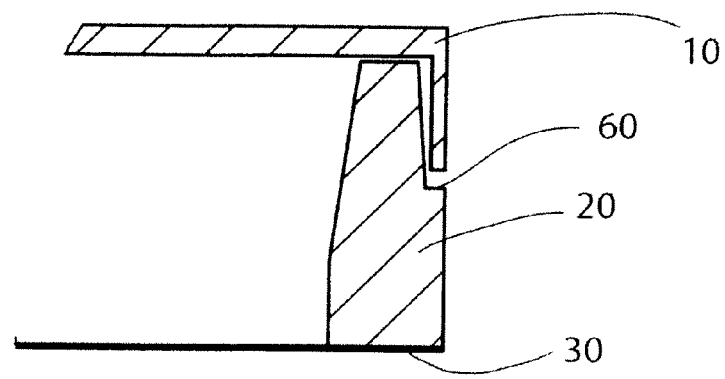

FIGS. 2a and 2b show cross-sectional views of the exemplary sample chamber of FIG. 1. FIG. 2a in particular shows a complete cross-section of the sample chamber, while in FIG. 2b, an enlarged view of the detail 70 of FIG. 2a is shown.

In FIG. 2a, the first component 20, the second component 30 and the lid 10 are shown again. The lid 10 is placed on the first component 20 in FIG. 2a. Here, the surrounding edge 60 is shown which permits the lid 10 to be placed upon it.

In FIG. 2b, the region 70 is shown in an enlarged view. The surface of the first component 20, which touches or contacts the second component 30 in this connected state, is designated as contact surface of the first component 20. This contact surface has been treated with a plasma, with plasma waste gas, and/or with a reactive gas before the components have been connected. The surface region of the second component 30, which is covered or touched by the first component 20, is referred to as contact surface of the second component 30. This contact surface can also be treated with a plasma, with plasma waste gas and/or with a reactive gas before the connection.

As an alternative or in addition, the contact surface of the second component 30 can be irradiated with UV light before being connected, in both cases, an even better connection between the components can be achieved.

Figure 3:
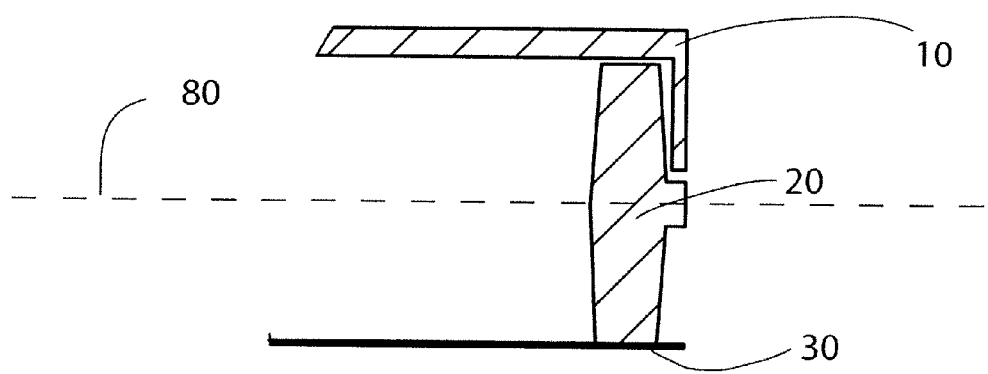
FIG. 3 shows a cross-sectional view of a further exemplary sample chamber.

FIG. 3 shows a detail of a cross-sectional view for a further exemplary sample chamber. This sample chamber, too, comprises a first component 20 consisting of an elastomer, and a second component 30. The second component 30 can be designed as described above, in particular, the second component 30 can be a cover glass with a thickness of 1 μm to 500 μm, in particular of 100 μm to 200 μm.

As in the previous examples, a contact surface of the first component 20 has been treated with a plasma, with plasma waste gas, and/or with a reactive gas before the connection of the components.

In this example, the first component 20 is designed to be mirror-symmetrical with respect to a plane of symmetry 80 that is parallel to the contact surface of the first component 20. This facilitates production, as during the production process, the second component 30 does not have to be applied to a certain side of the first component 20, but two equivalent surfaces are available for connection.

In FIG. 3, the plane of symmetry 80 is indicated as a dashed line for illustration purposes.

The contact surface of the second component 30 is in this example laterally surrounded by further surface regions of the second component 30 in other words, the contact surface of the second component 30 is not located at an edge of the second component 30. Moreover, the second component is in this example designed such that a part of the second component 30 in FIG. 3 projects beyond the outer side face of the first component 20.

As an alternative, the first component 20 can also project at least partially beyond a side face of the second component 30.

According to an alternative, the contact surface of the second component 30 could also be arranged at an edge of the second component 30. In this case, the side face of the first component 20 can in particular be aligned with a side face of the second component 30 after connection.

In the previous examples, the first component 20 consisted of an elastomer. As an alternative, however, the first component 20 could also comprise, apart from the elastomer, further materials. In particular, the first component 20 can additionally comprise a thermoplastic, in particular COC, COP, PE, PS, PC, and/or PMMA. In this case, however, the first component 20 is designed such that the elastomer is arranged at least in the region of the contact surface of the first component 20 which is treated with a plasma, with plasma waste gas, and/or with a reactive gas.

Figure 4:
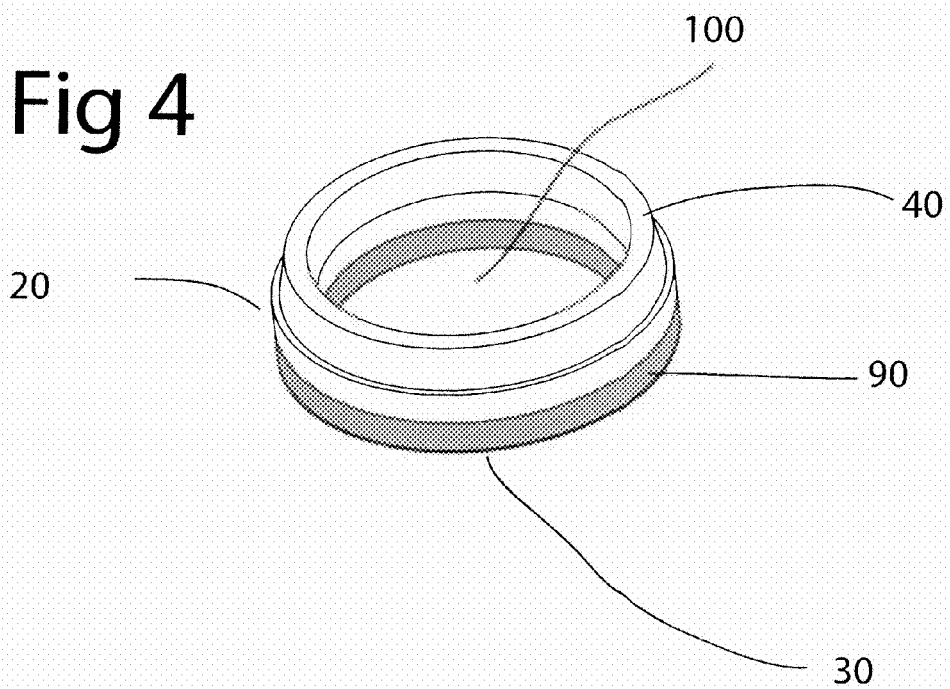
FIG. 4 shows a perspective view of a further exemplary sample chamber.

The first component 20 can also be a multi-component part. A corresponding example of a sample chamber is shown in FIG. 4.

In this example, the first component 20 comprises a first element 40 and a second element 90. The second element 90 comprises the elastomer or consists of an elastomer, while the first element 40 comprises a thermoplastic or consists of a thermoplastic. In this example, the first component 20 can have been manufactured in a two-component injection molding process.

The connection with the second component 30 was then effected as described in the above examples.

By the combination of a thermoplastic and an elastomer, the first component 20 can be more stable.

The dimension of the second element 90 in a direction perpendicular to the contact surface of the first component, which dimension is constant in this example, can be maximally 50%, in particular 1% to 20%, of the total dimension of the first component 20 perpendicular to the contact surface, said dimension being constant in this example.

In other words, the height of the second element 90 can be maximally half, in particular only 1% to 20%, of the total height of the first component 20.

By such an embodiment of the second element 90, the contact between a liquid disposed in a reservoir 100 formed by connecting the first component 20 with the second component 30 and the elastomer can be minimized. This is advantageous as the elastomer can tend to absorb liquids or discharge components into a liquid. So, by the low height of the second element 90, the risk of contamination in the liquid can be minimized.

Figure 5A:
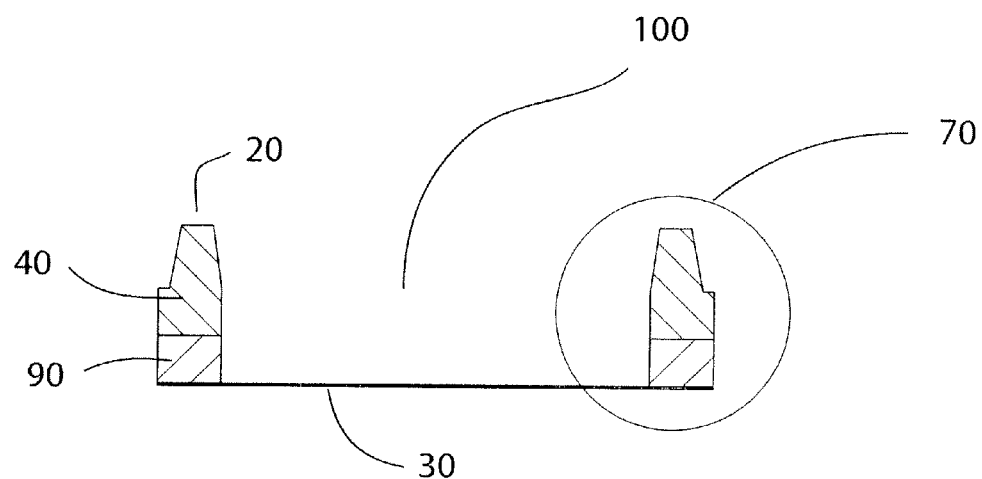
FIGS. 5a and 5b show cross-sectional views of the exemplary sample chamber of FIG. 4.
Figure 5B:
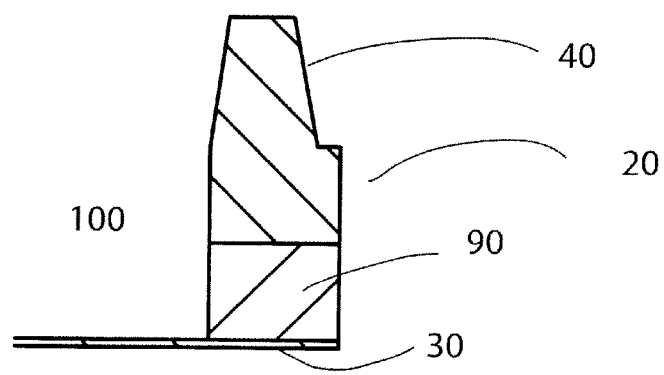

In FIGS. 5a and 5b, the exemplary sample chamber of FIG. 4 is shown again in cross-sectional views. In particular, FIG. 5b shows an enlarged view of the region 70 of FIG. 5a.

Figure 6A:
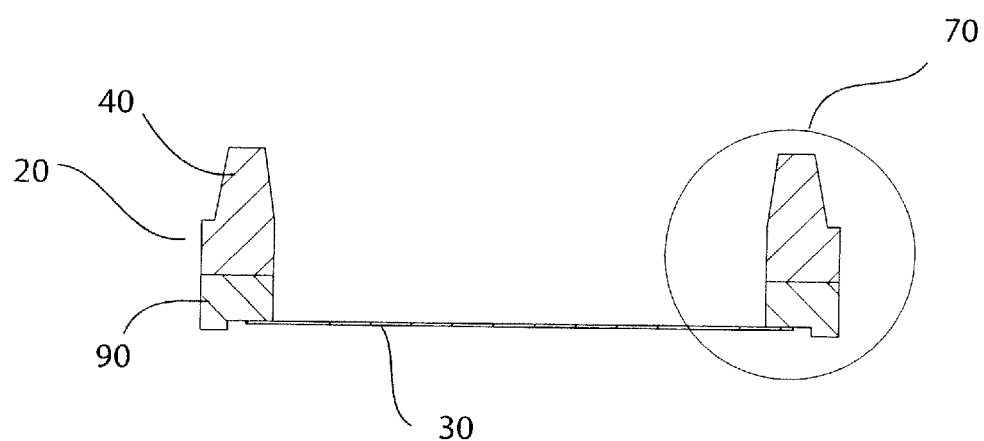
FIGS. 6a and 6b show cross-sectional views of a further exemplary sample chamber.
Figure 6B:
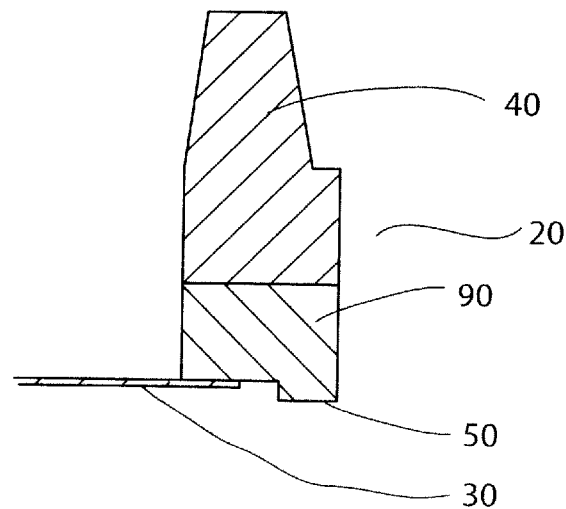

In FIGS. 6a and 6b, cross-sectional views of a further exemplary sample chamber are shown. In particular, FIG. 6b shows an enlarged representation of the region 70 of FIG. 6a. This sample chamber, too, comprises a first component 20 and a second component 30 which have been connected to each other as illustrated above. The first component 20 here comprises a first element 40 and a second element 90, the second element 90 comprising the elastomer or consisting of the elastomer.

As can be in particular seen in the detailed view in FIG. 5b, the first component 20, in particular the second element 90, is designed such that a part 50 of the first component 20 projects beyond a side face of the second component 30.

In this example, the part 50 also projects beyond a side of the second component 30 facing away from the contact surface of the second component 30. Thereby, the second component 30 can be protected from damages. This is in particular advantageous if the sample chambers are stored as bulk goods after they have been manufactured. This is particularly advantageous if the second component 30 comprises glass or consists of glass, as the elastomer cannot break the glass. By the part 50, glass-glass contacts in the bulk material can be avoided or reduced.

In the previous examples, the sample chamber comprised a reservoir 100 for receiving a liquid. However, two or more reservoirs can also be provided which are formed in particular by connecting the first component 20 with the second component 30. In particular, 12, 24, 48, 96, 384 or 1536 reservoirs can be provided.

Figure 7A:
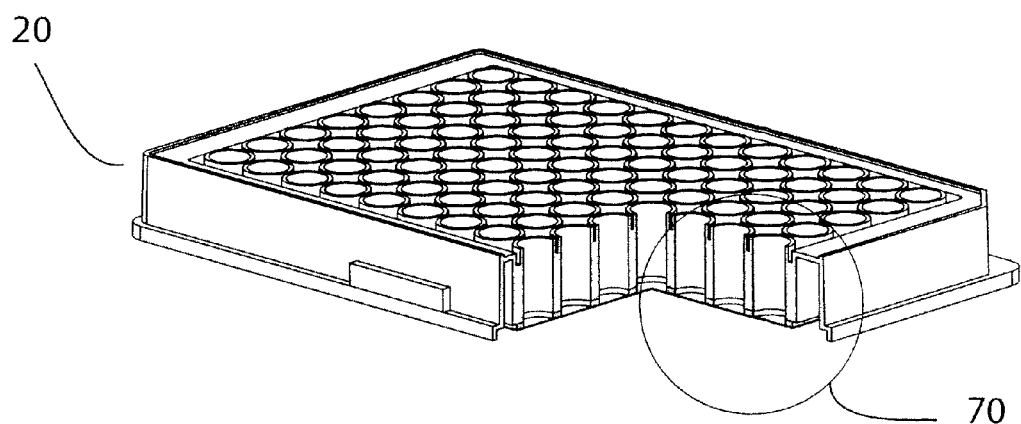
FIGS. 7a and 7b show perspective views of a further exemplary sample chamber.
Figure 7B:
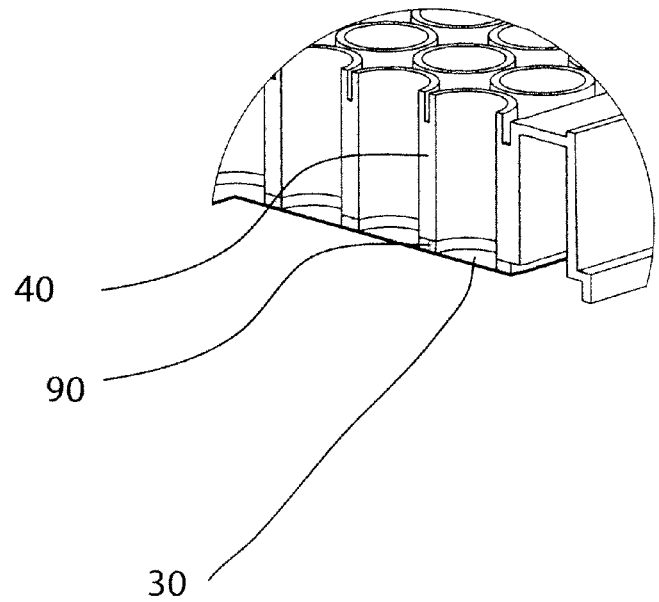

A corresponding example of a sample chamber with several reservoirs is shown in FIGS. 7a and 7b. In FIG. 7b, in particular a detailed view of the region 70 from FIG. 7a is shown.

This exemplary sample chamber, too, comprises a first component 20 and a second component 30 which have been connected to each other as illustrated above. In particular, the first component 20 comprises a first element 40 comprising a thermoplastic plastic, and a second element 90 comprising an elastomer or consisting of an elastomer. In the first component 20, a plurality of passage openings is formed which form, after the first component 20 has been connected with the second component 30, a plurality of reservoirs for receiving liquids.

Figure 8A:
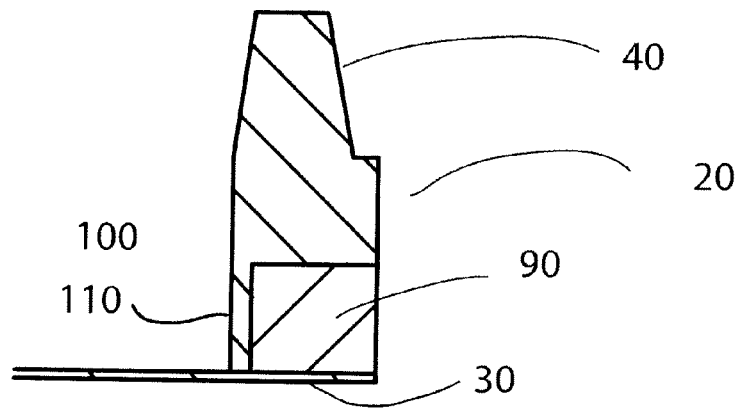
FIGS. 8a and 8b show cross-sectional views of further exemplary sample chambers.

In FIG. 8a, a cross-sectional view of a region of a further exemplary sample chamber is shown. The latter essentially corresponds to the sample chamber according to the view of FIG. 5b, in this case, the first element 40, however, is designed such that a part of the first element 40 at least partially covers the second element 90 towards the reservoir. For this, a region 110 of the first element 40 is provided which projects beyond the base of the first element 40. By this cover of the elastomer by the region 110, the risk of contamination for a liquid which is disposed in the reservoir 100 can be further reduced in this case, the first element 40 preferably consists of a thermoplastic, for example of COC, COP, PE, PS, PC, and/or PMMA.

The height of the region 110, that means the dimension in a direction perpendicular to the contact surface of the first component, is here preferably smaller than the height of the second element 90 to ensure a secure connection.

Figure 8B:
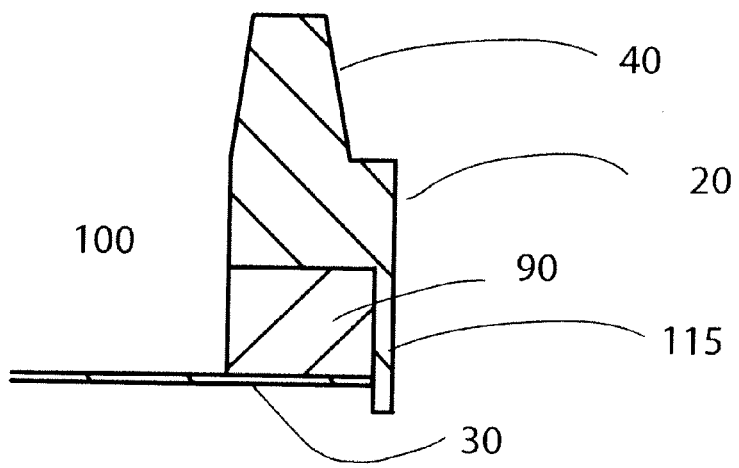

In FIG. 8b, a cross-sectional view of a region of a further exemplary sample chamber is shown. The latter essentially corresponds to the sample chamber according to the view of FIG. 5b. In this case, however, the first element 40 is designed such that a part of the first element 40 covers the second element 90 on a side facing away from the reservoir 100. For this, a region 115 of the first element 40 is provided which projects beyond the base of the first element 40. By the cover of the elastomer, the risk of damages can be reduced for the second element 90. In this case, the first element 40 preferably consists of a thermoplastic, for example of COC, COP, PE, PS, PC, and/or PMMA.

The height of the region 115, that means the dimension in a direction perpendicular to the contact surface of the first component, is here preferably higher than the height of the second element 90. Thereby, the second component 30 can also be at least partially protected from possible damages.

In the previous examples, two components 20 and 30 have been connected to each other for manufacturing the sample chamber. However, at least one further component can also be provided. For example, a third component can be provided which is in particular connected to the first component 20. For this, a further region of the first component 20, in which at least a part of the elastomer is arranged, can be treated with a plasma, with plasma waste gas, and/or with a reactive gas. At least a part of this treated region can then be connected with the third component.

In the shown examples, the first component 20 forms a side wall and the second component 30 forms a bottom of a reservoir 100 after they have been connected. However, it is also conceivable that the first component 20 forms a bottom and the second component 30 forms a side wall of a reservoir after they have been connected. A corresponding example is shown in FIG. 9.

Figure 9:
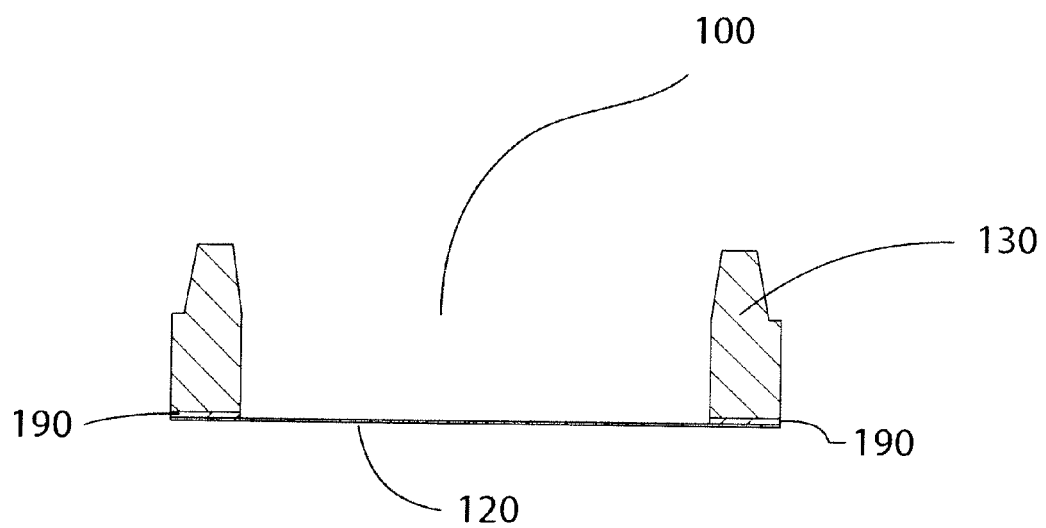
FIG. 9 shows a cross-sectional view of a further exemplary sample chamber.

In FIG. 9, an exemplary sample chamber is shown, comprising a first component 120 comprising an elastomer in the region 190. The elastomer can here be arranged on a plastic plate. The elastomer in the contact region 190 is then treated with a plasma, with plasma waste gas, and/or with a reactive gas.

The second component 130 can consist of glass or be coated with glass in the contact region with the elastomer. Said second component 130 is then pressed against the first component 120 whereby a firm connection of the components can be achieved.

It will be understood that features mentioned in the above described embodiments are not restricted to these special combinations and are also possible in any other combinations. Moreover, the geometry of the reservoirs or of the sample chambers is not restricted to the square shape shown in the figures. Any other geometries are also possible, such as channels which are formed by connecting a first component with corresponding recesses with a second component.

The invention claimed is:

1. Method of manufacturing a sample chamber, comprising the steps of:
    providing a first and a second component, the first component comprising an elastomer;
    treating the elastomer in the region of a contact surface of the first component and/or treating a contact surface of the second component with a plasma, with plasma waste gas, and/or with a reactive gas; and
    connecting the contact surface f the first component with the contact surface of the second component;
    wherein by the connection of the first and the second components, a reservoir is obtained, where the first component forms a side wall or a bottom of the reservoir, where the first component comprises a first element and a second element connected thereto, where only the second element comprises the elastomer, and where the first element is arranged such that it at least partially covers the second element towards the reservoir.

2. Method according to claim 1, wherein the first component is designed such that a part of the first component in which a part of the elastomer is arranged projects beyond a side face of the second component after the connection of the first with the second component.

3. Method according to claim 2, wherein the part is designed such that, after the connection, it extends into a direction perpendicular to the contact surface of the first component, in particular in such a way that a side face of the second component is at least partially covered or overlapped.

4. Method according to claim 2, wherein the part is designed such that it projects, after the connection, beyond a side of the second component facing away from the contact surface of the second component.

5. Method according to claim 1, wherein the first component moreover comprises a thermoplastic.

6. Method according to claim 5, wherein the first element comprises the thermoplastic.

7. Method according to claim 6, wherein the maximum or mean dimension of the second element in a direction perpendicular to the contact surface of the first component amounts to maximally 50%, in particular 1% to 20%, of the total maximal or mean dimension of the first component perpendicular to the contact surface of the first component.

8. Method according to claim 1, wherein the thickness of the first component can be smaller in a region which comprises at least one part of the elastomer or consists of at least one part of the elastomer, than the mean thickness of the first component.

9. Method according to claim 1, comprising an irradiation of the contact surface of the second component with UV light.

10. Method according to claim 1, wherein the second component comprises, at least in the region of the contact surface of the second component, a glass.

11. Method according to claim 1 wherein the elastomer comprises a silicone, in particular polydimethylsiloxane, PDMS.

12. Method according to claim 1, wherein the eiastomer has a Shore A hardness of more than 40, in particular of 60 to 80.

13. Sample chamber for microscopic examinations, obtained by a method according to claim 1.

* * * * *